US011395754B2

(12) United States Patent
Wisse et al.

(10) Patent No.: US 11,395,754 B2
(45) Date of Patent: Jul. 26, 2022

(54) WEARABLE SUPPORT STRUCTURE FOR AT LEAST PARTLY RELIEVING A HUMAN BODY DURING LEANING OR BENDING OVER

(71) Applicant: Laevo B.V., Delft (NL)

(72) Inventors: Boudewijn Martin Wisse, Delft (NL); Michael Martinus Hölscher, Delft (NL)

(73) Assignee: Laevo B.V., Delft (NL)

( * ) Notice: Subject to any disclaimer, the term of this patent is extended or adjusted under 35 U.S.C. 154(b) by 277 days.

(21) Appl. No.: 16/604,326

(22) PCT Filed: Apr. 17, 2018

(86) PCT No.: PCT/NL2018/050238
§ 371 (c)(1),
(2) Date: Oct. 10, 2019

(87) PCT Pub. No.: WO2018/194447
PCT Pub. Date: Oct. 25, 2018

(65) Prior Publication Data
US 2020/0069453 A1 Mar. 5, 2020

(30) Foreign Application Priority Data
Apr. 18, 2017 (NL) .................................... 2018730

(51) Int. Cl.
*A61F 5/02* (2006.01)
*A61F 5/01* (2006.01)

(52) U.S. Cl.
CPC ............ *A61F 5/028* (2013.01); *A61F 5/0104* (2013.01)

(58) Field of Classification Search
CPC .. A61F 5/02; A61F 5/022; A61F 5/024; A61F 5/026; A61F 5/028; A61F 5/104;
(Continued)

(56) References Cited

U.S. PATENT DOCUMENTS

| 8,568,344 B2 * | 10/2013 | Ferguson ............. A61H 1/0244 602/16 |
| 2008/0228121 A1 | 9/2008 | Hughes |
| 2010/0069806 A1 | 3/2010 | Jinright |

FOREIGN PATENT DOCUMENTS

| DE | 19652416 A1 | 6/1998 |
| NL | 2014451 B1 | 10/2016 |

(Continued)

OTHER PUBLICATIONS

International Search Report for International Application No. PCT/NL2018/050328, dated Jun. 25, 2018 (4 pages).

(Continued)

*Primary Examiner* — Keri J Nelson
(74) *Attorney, Agent, or Firm* — Nixon Peabody LLP (57) ABSTRACT

Wearable support structure for at least partly relieving a human body during leaning or bending over, said structure comprising a frame having a chest support, pivoting arrangements for pivoting the support structure in correspondence with the leaning or bending or the human body, an elongated stay connected to said chest support, a lumbar support, connected to said pivoting arrangements, and arranged for bearing upon a lumbar area of said human body, and a thigh support, connected to said pivoting arrangements, and arranged for bearing upon a front side of a thigh area of said human body. The wearable support structure comprises a connecting device for detachably connecting at least one of: said thigh support to said pivoting arrangements; said elongated stay to said chest support; and said elongated stay to said pivoting arrangements.

16 Claims, 4 Drawing Sheets

(58) Field of Classification Search
CPC ...... A61F 2005/0155; A61F 2005/0179; A61F 2005/0197; A61F 5/0104
See application file for complete search history.

(56) References Cited

FOREIGN PATENT DOCUMENTS

| WO | WO 2015/041532 A1 | 3/2015 |
| WO | WO 2016/148566 A1 | 9/2016 |

OTHER PUBLICATIONS

Written Opinion of International Searching Authority for International Application No. PCT/NL2018/050238, dated Jun. 25, 2018 (5 pages).

\* cited by examiner

WEARABLE SUPPORT STRUCTURE FOR AT LEAST PARTLY RELIEVING A HUMAN BODY DURING LEANING OR BENDING OVER

CROSS-REFERENCE TO RELATED APPLICATION

This application is a national stage of Application No. PCT/NL2018/050238 filed Apr. 17, 2018, which claims priority from Netherlands Application No. 2018730 filed Apr. 18, 2017, which are both incorporated by reference in their entireties.

The present disclosure relates to a wearable support structure for at least partly relieving a human body during leaning or bending over, said structure comprising a frame having:
- a chest support for bearing upon a chest of said human body;
- pivoting arrangements for pivoting the support structure in correspondence with the leaning or bending or the human body;
- an elongated stay connected to said chest support, provided to extend substantially alongside said human body and connected to said pivoting arrangements,
- wherein said stay is arranged such that said stay is in a first state corresponding with an upright position of said human body when being unloaded, and arranged to be biased back to said first state when being into a second state corresponding with a leaning or bending position of said human body,
- a lumbar support, connected to said pivoting arrangements, and arranged for bearing upon a lumbar area of said human body, and
- a thigh support, connected to said pivoting arrangements, and arranged for bearing upon a front side of a thigh area of said human body.

Patent application number NL2014451 discloses such a wearable support structure. One of the down downsides of such a wearable support structure is that it is relatively difficult to adapt the wearable support for different users.

An object of the present invention is to provide for a wearable support structure that is relatively easy to adapt for different users.

The object is achieved by the wearable support structure according to claim 1. The wearable support structure according to the present invention comprises a connecting device for detachably connecting at least one of:
- said thigh support to said pivoting arrangements;
- said elongated stay to said chest support; and
- said elongated stay to said pivoting arrangements.

An additional advantage of the wearable support structure according to the current disclosure is it is cheaper to transport. The known wearable support structure is relatively voluminous and thereby relatively expensive to transport. By detaching at least one of the parts according to claim 1 the packaging volume of a wearable support structure is reduced. A reduced volume allows for more wearable support structures to be packed in a similar volume thereby lowering the transport cost for a wearable support structure. Moreover, the wearable support structure allows for a relative easy repair of the support structure. If one of the parts that are detachably connected to the frame are in need of replacement a user can relatively easily replace such a part in a relatively short time and without special tooling.

It is beneficial if said connecting device comprises a first connecting element and a second connecting element, wherein said first connecting element is arranged for rigid connection to a first part of said wearable support structure that is at least one of said pivoting arrangements and said chest support, wherein said second connecting element is arranged for rigid connection to a second part of said wearable support structure that is at least one of said thigh support and said stay, wherein said first connecting element comprises a receiving wall that is at least partly surrounding a receiving space for partly receiving said second connecting element. By receiving said second connecting element at least partly in a receiving space of said first connecting element, said second connecting element is partly integrated upon connection in said first connecting element.

In this regard it is advantageous if said connecting device comprises a blocking unit, wherein said blocking unit in a first state thereof blocks detachment of said first connecting element from said second connecting element and wherein in a second state of said blocking unit said first connecting element is detachable from said second connecting element. The blocking unit allows for a blocking of said second connection element while being in said partly integrated position for blocking detachment of said connection between said first and second connecting elements. As such, by changing the state of the blocking unit said first connecting element and said second connecting element can be detached or blocked for detachment relatively easily to allow for adaption of the wearable support structure known from NL2014451 by exchanging parts such as a stay or a thigh support.

In an embodiment of the wearable support structure according to the present disclosure said first connecting element and said second connecting element, while connected, extend in a longitudinal direction, wherein said connecting device comprises a rotation organ for allowing said first connecting element, while connected to said second connecting element, to rotate about a predetermined angle relative to said second connecting element about a common rotation axis extending in said longitudinal direction. In other words, for allowing said first connecting element, while connected to said second connecting element, to rotate in a co-axial manner about said common rotation axis about said predetermined angle. This advantageous to realise an improved freedom of movement when wearing the known wearable support structure.

In this regard it is beneficial if said predetermined angle is in the range of 60-120 degrees, preferably in the range of 80-100 degrees. An angle in this specific range is beneficial for realizing an improved freedom of movement while maintaining support, by said support structure, of said human body.

In a practical embodiment of the wearable support structure according to the present disclosure said rotation organ comprises a recess provided in one of said first connecting element and said second connecting element, wherein said blocking unit in said first state of said blocking unit is at least partly received in said recess for said blocking, wherein said blocking unit is arranged to be moveable in said recess for allowing said rotation about said common rotation axis about said predetermined angle. This is a practical way for realising blocking of detachment of said first connecting element from said second connecting element while allowing for rotation about a common rotation axis.

It is beneficial if said connecting device comprises a distance organ for connecting said first part of said wearable support structure at a predetermined distance from said second part of said wearable support structure. This is beneficial to allow for a detachable connection of parts of the wearable support structure wherein after detaching and connecting of parts said distance is predetermined such that the geometry of the wearable support structure is predictable to avoid the need to adapt the wearable support structure.

It is preferred if said distance organ comprises said recess for connecting said first part of said wearable support structure at said predetermined distance from said second part of said wearable support structure. This is preferable to realise a connecting element having a relatively low amount of components while allowing for said rotation and said connecting at said predetermined distance.

In a preferred embodiment of the connecting device said distance organ is arranged for connecting said first part of said wearable support structure at a further predetermined distance from said second part of said wearable support structure. This is beneficial to allow for a relative easy adaption of the wearable support structure to the length of the body of the user of the wearable support structure.

In this regard it is beneficial if said distance organ is provided with a further recess, wherein said further recess is provided in one of said first connecting element and said second connecting element, wherein said blocking unit in said first state of said blocking unit is at least partly received in said further recess for connecting said first part of said wearable support structure at said further predetermined distance from said second part of said wearable support structure. This is beneficial to realise a connecting element having a relatively low amount of components while allowing for said rotation at said predetermined distance and said connecting at said further predetermined distance.

In an embodiment of the connecting device said blocking unit is arranged to be moveable in said further recess for allowing said rotation about said common rotation axis about said predetermined angle. This is beneficial to realise a connecting element having a relatively low amount of components while allowing for said rotation at said predetermined distance and said predetermined distance.

It is beneficial if said connecting device comprises an actuation element that is movable to a first position wherein said blocking unit is in said second state upon actuation of said actuation element. This is beneficial to operate the blocking unit in a practical way.

In a practical embodiment of the connecting device according to the present disclosure, said receiving wall is provided with a receiving wall opening, wherein said blocking unit comprises a blocking element that is movably arranged in said receiving wall opening, wherein in a first position of said blocking element said blocking unit is in said first state and wherein in a second position of said blocking element said blocking unit is in said second state. This embodiment is preferred since it allows to realise a connecting element having a relatively low amount of components while allowing a reliable blocking for detachment and detachment.

In a practical embodiment of the wearable support structure according to the present disclosure, said wearable support structure further comprises at least one of:
  an arm support arranged for supporting an arm of said human body, wherein said arm support is detachably connected, by said connecting device, to said frame;
  a leg support, preferably comprising a knee joint, for supporting a leg of said human body, wherein said leg support is detachably connected, by said connecting device, to said frame;
  a head support arranged for supporting a head of said human body, wherein said head support is detachably connected, by said connecting device, to said frame;
  a tool support arranged for supporting a tool, wherein said tool support is detachably connected, by said connecting device, to said frame.

In a preferred embodiment of the wearable support structure according to the present disclosure said frame comprises:
  a further elongated stay connected to said chest support, wherein said elongated stay and said further elongated stay are provided to extend substantially alongside opposite sides of said human body and connected to said pivoting arrangements,
  wherein said elongated stay and said further elongated stay are resilient stays arranged such that they are in said first state corresponding with an upright position of said human body when being unloaded, and arranged to be biased back to said first state when being bent into said second state corresponding with a leaning or bending position of said human body, wherein said elongated stay and said further elongated stay in said first state are in a stretched state and in said second state are in a bent state. This is beneficial for providing a wearable support structure which is able to support more freedom of movement for a user, while providing support while leaning forward or bending over, but also during squatting, reaching, crawling, or working from on your knees.

In this regard it is preferable if said chest support comprises two spatially separated pivoting means, wherein said elongated stay and said further elongated stay are each detachably connected, by said connecting device, to said chest support via a different one of said pivoting means, wherein each of said pivoting means is arranged to pivot said chest support with respect to a stay connected thereto, in a plane substantially parallel to said chest of said human body. By making the chest support pivotable with respect to a stay connected thereto, it is facilitated that a user wearing the structure has a large freedom of movement. More specifically, the upper body of the user, i.e. the human torso, is for example able to freely move laterally/sideways. A user wearing the wearable support structure thus has more freedom in their lateral movement, as the lateral movement is supported by the pivoting means in combination with the chest support. An advantage of this preferred embodiment of the wearable support structure according to the present disclosure is that it better facilitates a twisting and bending over movement, or a bending and then a twisting movement, of the human body. Another advantage of this preferred embodiment is that, in case a user bends to the left, the chest support turns away from the right shoulder or armpit. This is advantageous as the right arm can then be used to reach to the left without the chest support being in the way. The same is of course true when the user bends to the right, but then vice versa. The combination of the chest support, the two elongated stays and the pivoting arrangements in fact resembles a part of a parallelogram, wherein the stays and the chest support can move in a plane defined by the parallelogram and with respect to the pivoting arrangements.

In an embodiment of the wearable support structure according to the present disclosure said two elongated stays are rotatably connected to said pivoting arrangements such that the connecting ends of each of said elongated stays is rotatable around its elongated axis. Typically, a user will not only just bend forward or just lean sideways but their movement will consist of a combination of directions. It is often a combination of a rotation, for example a trunk rotation, and a bending aspect. By rotatably connecting the connecting ends of each of the elongated stays to the pivoting arrangements, the rotating movement of the torso of the user, i.e. the trunk rotation, is more efficiently supported. To put it differently, the connecting ends rotate around a vertical axis, which runs from the top to the bottom of the human body. For example, when a gymnast performs a three hundred and sixty degree turn, they're rotating around the vertical axis.

The described aspects of the wearable support structure also apply to:

Clause 1: A wearable support structure for at least partly relieving a human body during leaning or bending over, said structure comprising a frame having:
- a chest support for bearing upon a chest of said human body;
- an elongated stay connected to said chest support, provided to extend substantially alongside said human body;
- wherein said stay is arranged such that said stay is in a first state corresponding with an upright position of said human body when being unloaded, and arranged to be biased back to said first state when being into a second state corresponding with a leaning or bending position of said human body,
- a lumbar support arranged for bearing upon a lumbar area of said human body, and
- a thigh support arranged for bearing upon a front side of a thigh area of said human body, characterized in that said wearable support comprises a connecting device for detachably connecting at least one of:
- said elongated stay to said chest support; and
- said elongated stay to said thigh support.

Clause 2. Wearable support structure according to clause 1, wherein said connecting device comprises a first connecting element and a second connecting element,
- wherein said first connecting element is arranged for rigid connection to a first part of said wearable support structure that is at least said chest support and said stay,
- wherein said second connecting element is arranged for rigid connection to a second part of said wearable support structure that is at least said thigh support and said stay,
- wherein said first connecting element comprises a receiving wall that is at least partly surrounding a receiving space for partly receiving said second connecting element.

Clause 3. Wearable support structure according to clause 2, wherein said connecting device comprises a blocking unit, wherein said blocking unit in a first state thereof blocks detachment of said first connecting element from said second connecting element and wherein in a second state of said blocking unit said first connecting element is detachable from said second connecting element.

Clause 4. Wearable support structure according to clause 2 or clause 3, wherein said first connecting element and said second connecting element, while connected, extend in a longitudinal direction, wherein said connecting device comprises a rotation organ for allowing said first connecting element, while connected to said second connecting element, to rotate about a predetermined angle relative to said second connecting element about a common rotation axis extending in said longitudinal direction.

Clause 5. Wearable support structure according to clause 4, wherein said predetermined angle is in the range of 60-120 degrees, preferably in the range of 80-100 degrees.

Clause 6. Wearable support structure according to clause 4 or 5, wherein said rotation organ comprises a recess provided in one of said first connecting element and said second connecting element, wherein said blocking unit in said first state of said blocking unit is at least partly received in said recess for said blocking, wherein said blocking unit is arranged to be moveable in said recess for allowing said rotation about said common rotation axis about said predetermined angle.

Clause 7. Wearable support structure according to any one of the preceding clauses, wherein said connecting device comprises a distance organ for connecting said first part of said wearable support structure at a predetermined distance from said second part of said wearable support structure.

Clause 8. Wearable support structure according to clause 6 and 7, wherein said distance organ comprises said recess for connecting said first part of said wearable support structure at said predetermined distance from said second part of said wearable support structure.

Clause 9. Wearable support structure according to clause 7 or 8, wherein said distance organ is arranged for connecting said first part of said wearable support structure at a further predetermined distance from said second part of said wearable support structure.

Clause 10. Wearable support structure according to clause 9, wherein said distance organ is provided with a further recess, wherein said further recess is provided in one of said first connecting element and said second connecting element, wherein said blocking unit in said first state of said blocking unit is at least partly received in said further recess for connecting said first part of said wearable support structure at said further predetermined distance from said second part of said wearable support structure.

Clause 11. Wearable support structure according to clause 4 and 10, wherein said blocking unit is arranged to be moveable in said further recess for allowing said rotation about said common rotation axis about said predetermined angle.

Clause 12. Wearable support structure according to any one of the preceding clauses, wherein said connecting device comprises an actuation element that is movable to a first position wherein said blocking unit is in said second state upon actuation of said actuation element.

Clause 13. Wearable support structure according to any one of the preceding clauses, wherein said receiving wall is provided with a receiving wall opening, wherein said blocking unit comprises a blocking element that is movably arranged in said receiving wall opening, wherein in a first position of said blocking element said blocking unit is in said first state and wherein in a second position of said blocking element said blocking unit is in said second state.

Clause 14. Wearable support structure according to any one of the preceding clauses, wherein said wearable support structure further comprises at least one of:
- an arm support arranged for supporting an arm of said human body, wherein said arm support is detachably connected, by said connecting device, to said frame;
- a leg support, preferably comprising a knee joint, for supporting a leg of said human body, wherein said leg support is detachably connected, by said connecting device, to said frame;
- a head support arranged for supporting a head of said human body, wherein said head support is detachably connected, by said connecting device, to said frame;
- a tool support arranged for supporting a tool, wherein said tool support is detachably connected, by said connecting device, to said frame; and pivoting arrangements for pivoting the support structure in correspondence with the leaning or bending or the human body, wherein said pivoting arrangements is detachably connected, by said connecting device to at least one of said elongated stay and said thigh support.

Clause 15. Wearable support structure according to any one of the preceding clauses, wherein said frame comprises:
  a further elongated stay connected to said chest support, wherein said elongated stay and said further elongated stay are provided to extend substantially alongside opposite sides of said human body;
  wherein said elongated stay and said further elongated stay are resilient stays arranged such that they are in said first state corresponding with an upright position of said human body when being unloaded, and arranged to be biased back to said first state when being bent into said second state corresponding with a leaning or bending position of said human body, wherein said elongated stay and said further elongated stay in said first state are in a stretched state and in in said second state are in a bent state.

Clause 16. Wearable support structure according to clause 15, wherein said chest support comprises two spatially separated pivoting means, wherein said elongated stay and said further elongated stay are each detachably connected, by said connecting device, to said chest support via a different one of said pivoting means, wherein each of said pivoting means is arranged to pivot said chest support with respect to a stay connected thereto, in a plane substantially parallel to said chest of said human body.

The present invention will now be explained by means of a description of a preferred embodiment a connecting device according to the present invention and a wearable support structure comprising a connecting device according to the present invention, in which reference is made to the following schematic figures, in which.

The support structure 201 comprises a frame having a chest support 202 for bearing upon a chest of said human body. Pivoting arrangements 207 are provided for pivoting the support structure 201 in correspondence with the leaning or bending or the human body. The frame further comprises two elongated stays 203a, 203b connected to the chest support 202, which stays 203a, 203b are provided to extend substantially alongside opposite sides of the human body and connect to the pivoting arrangements 207. In use a first stay 203a of support structure 201 will extend alongside the right side of the human body, whereas a second stay 203b will extend alongside the left side of the human body. However, the invention is not limited to this arrangement of the stays. Alternatively, the support structure can be provided with only one stay or more than two stays. Furthermore it is possible to arrange said stay or more stays at various positions different from the positions shown in FIG. 7. A support structure with one stay could be arranged such that the stay, in use, extends along the back of the human body.

Figure 7:
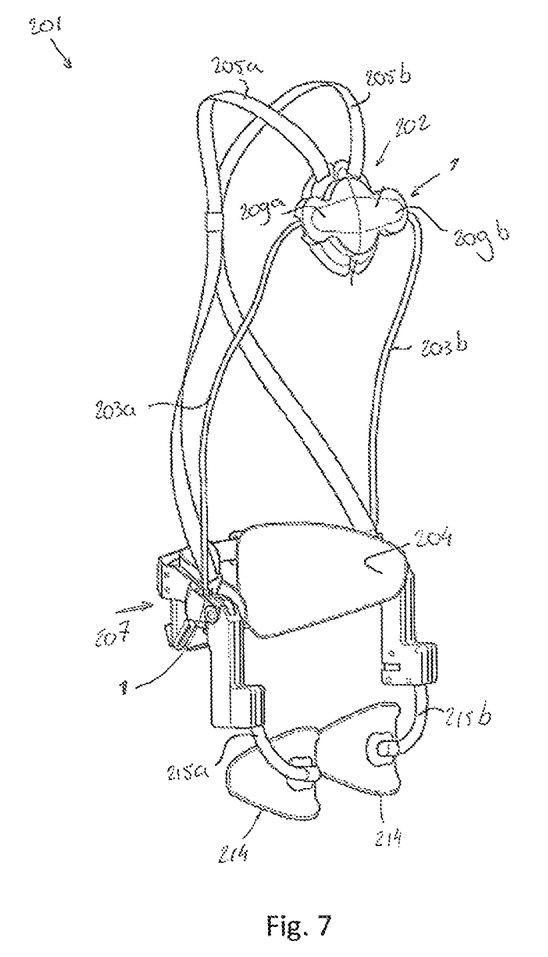
FIG. 7 shows a wearable support structure provided with a connecting device according to the present invention.

The stays 203a, 203b are resilient stays arranged such that they are in a stretched state corresponding with an upright position of said human body when being unloaded, and arranged to be biased back to said stretched state when being bent into a bent state corresponding with a leaning or bending position of the human body. The stays 203a, 203b may be substantially strip shaped, having a three-dimensional curved shape, the strip having for example a flat, curved, triangular or multi angular, round or oval cross section, which may be constant over the length of the stay or can vary along its length.

The frame further comprises a lumbar support 204, connected to said pivoting arrangements 207, and arranged for bearing upon a lumbar area of said human body, and comprises a thigh support 214, connected to said pivoting arrangements 207 via lower stays 215a, 215b, and arranged for bearing upon a front side of a thigh area.

The chest support 202 comprises two spatially separated pivoting means 209a, 209b, wherein said stays 203a, 203b are each connected to said chest support 202 support via a different one of said pivoting means 209a, 209b, wherein each of said pivoting means 209a, 209b is arranged to pivot said chest support 202 with respect to a stay 203a, 203b connected thereto, in a plane substantially parallel to said chest of said human body.

Shoulder bands 205a, 205b are provided, which shoulder bands 205a, 205b are to be placed over shoulders of said human body, and to be connected to the chest support 202 for retaining said chest support 202 to the chest of the human body.

The stays 203a, 203b are connected to said chest support 202 via a second embodiment of a connecting device 101 at one end of the stays 203a, 203b and connected to the pivoting means 207 via a first embodiment of the connecting device 1. The thigh support 214 is connected through lowers stays 215a, 215b to the pivoting arrangements 207 via the first embodiment of the connecting device 1. These embodiments of the connecting device 1, 101 will be explained in more detail further below.

The connecting device 1 shown in FIGS. 1-4 allows for detachably connecting two parts of a wearable support structure 201 such as the stays 203a, 203b and the pivoting arrangements 207.

Figure 1:
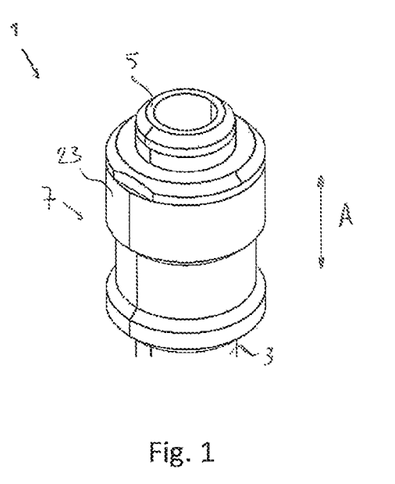
FIG. 1 shows a preferred embodiment of a connecting device according to the present invention.
Figure 2:
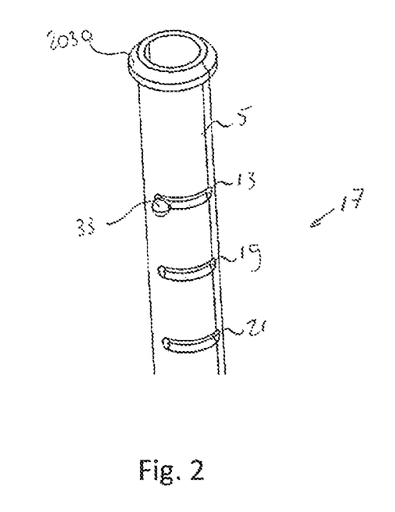
FIG. 2 shows parts of the preferred embodiment from FIG. 1.
Figure 3:
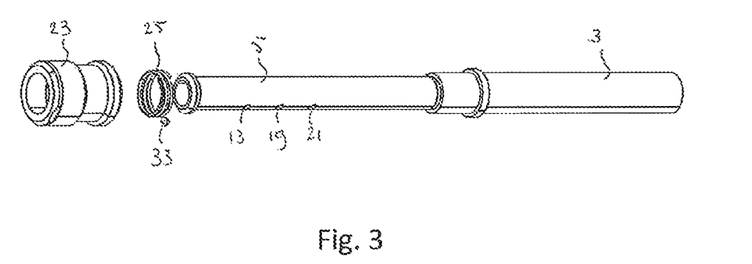
FIG. 3 shows parts of the preferred embodiment from FIG. 1.

Connecting device 1 has a first connector 3 and a second connector 5. The first connector 3, having a tube-shaped form extending in a longitudinal direction A, is rigidly connect to the pivoting arrangements 207. The second connector 5 is rigidly connected to an end of the stay 203a. The second connector as shown in FIG. 2 is a substantially rigid hollow tube. The wall of the tube is relatively thick so as to allow recesses 13, 19, 21 to be present in the wall without piercing the wall of the hollow tube. The recesses 13, 19 and 21 are gutter-like grooves in the outer wall of the connector 5 that extend along the wall of the connector in a direction perpendicular to the longitudinal direction A. The gutter-like grooves extent along about a quarter of the circumference of the connector 5 to allow in use a rotation of the first connector 3 of about 90 degrees with respect to the second connector 5. The second connector 5 is provided with a blocking unit comprising a blocking element formed by a ball-shaped element 33. Alternative forms of the blocking element are conceivable such as a cylinder shaped element. In a connected state of the first connector 3 and the second connector 5, the ball 33 is received in one of the gutter-like grooves 13, 19, 21. By positioning the ball in a particular groove 13, 19, 21 the distance between the stay 203a and the pivoting arrangements 207 can be determined. For instance for a user being gifted with a relative long body the ball 33 is received in the lower groove 21 as shown in FIG. 2. In this situation the second connector 5 is received in the receiving connector 3 only for a small part. A user of relative short height will position the second connector 5 relative to the first connector 3 such that the ball 33 is received in recess 19 or even 15 for yet smaller people.

Figure 4:
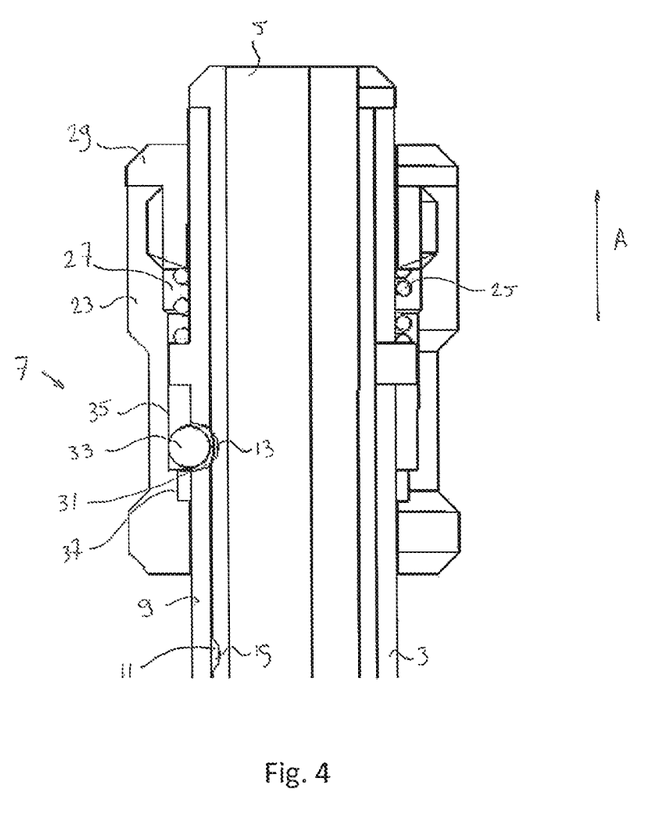
FIG. 4 shows a cross-section of the preferred embodiment from FIG. 1.

Ball 33 is dimensioned such that it is at least partly receivable in said grooves 13, 19, 21 and movable along length of the groove 13 extending perpendicular to said longitudinal direction A. In addition, ball 33 is also movable in a receiving wall opening 31 in a receiving wall 9 at least partly surrounding a receiving space 11 for partly receiving said second connector 5. As such ball 33 is movable in a radial direction of the tube-shaped connector 3 and thereby locked, at least substantially for displacement of the ball 33 in a tangential direction of the second connector perpendicular to the radial direction and the longitudinal direction A. The receiving wall opening 31 has a smaller diameter at the end of the receiving wall opening 9 exiting at the receiving wall opening than a diameter of the ball 33. This smaller diameter of the receiving wall opening 31 prevents the ball 33 from completely exiting the receiving wall opening 31 into the receiving space 11. Ball 33 can be displaced to a second position, as shown in FIG. 4, by pushing the actuation element 23 formed by a ring-shaped grip in the direction away from the stay 203 the ring 23 is brought in a first position. The ring 23 needs to be actively pushed towards this first position against the force of an urging element formed by a spring 25. In the first position of the ring 23, the ball 33 can either be at least partly inside the groove 13 or be pushed partly through the opening 31 in the receiving wall 11 by moving the second connector 5 such that the groove 13 no longer aligns with the ball 33. Upon releasing the ring 23 the ring moves back in the direction towards the stay, ie. in a direction corresponding with the top of the page of FIG. 4. Grip 23 is provided with a receiving recess 35 for at least partly receiving the ball 33 when the grip is pushed away from the stay 203a. In this actuated position of the grip 23 the ball can move into the receiving recess until it collides with a wall of receiving recess 35. If grip 23 is not actuated the ball 33 is forced into the receiving wall opening 31 by blocking wall 37. Blocking wall 37 is situated at a closer distance to said receiving wall opening 31 than said wall of the receiving recess to actively push ball 33 further into the receiving wall opening 31 when grip 23 is urged back by spring 25. In this position ball 33 is locked against blocking wall 37 when ball 33 is at least partly received in a groove 13, 19, 21 thereby blocking detachment of the stay 203a from the pivoting arrangements 207. Grip 23 is provided with a holding element formed by a donut-shaped plug 29 for substantially closing an receiving space 27 for holding said spring 25.

Figure 5:
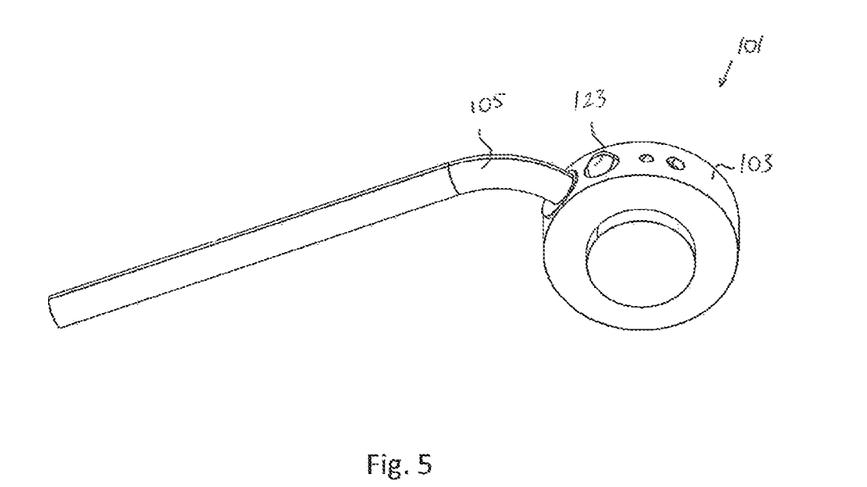
FIG. 5 shows another preferred embodiment of a connecting device according to the present invention.
Figure 6:
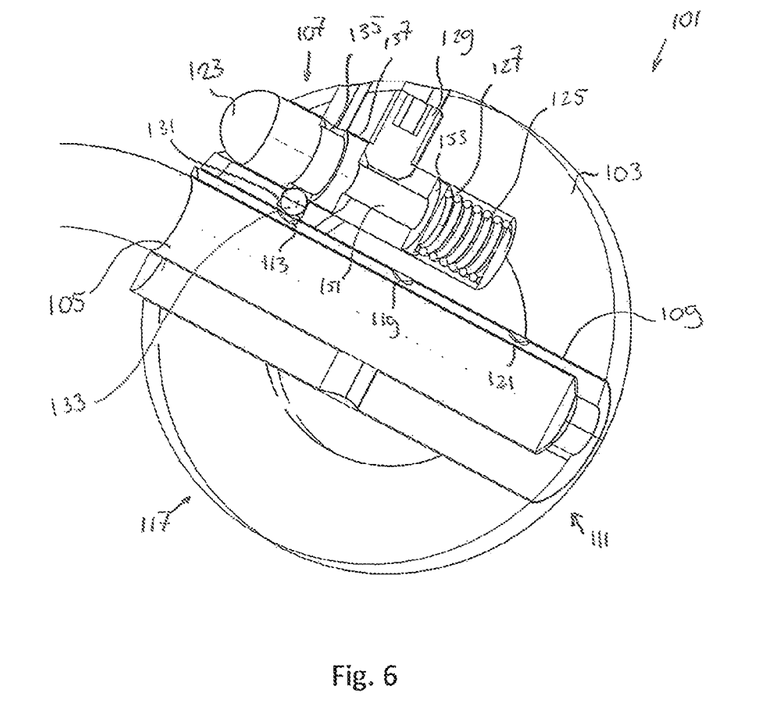
FIG. 6 shows a cross-section of the preferred embodiment from FIG. 5.

The connecting device 101 shown in FIGS. 5 and 6 differs mainly from the device 1 from FIGS. 1-4 in that the first connector 103 is not arranged for rotation with respect to the second connector 105 and in that the arrangement of the actuation element 123 differs. Reference numerals of parts of connecting device 101 similar, or at least functionally similar, to parts of the connecting device 1 are identified by reference numerals raised by 100.

The actuation element of device 101 is provided as a push button 123 partly received in receiving space 127. Button 123 can be pushed against the force of spring 125 to allow detachment of the first connector 3 from the second connector 5. Button 123 is provided with a stem 151 and a foot 153 extending in said receiving space 127. Holding element formed by a screw 129 screwed in a hole in the outer wall of the second connector 105 can be screwed such that a lower part of the screw 129 extends into the receiving space 127 as shown in FIG. 6. Button 123 is prevented from being pushed out of the second connector 105, by said spring 125, in that the for 153 will collide with the part of the screw 129 extending in said receiving space 127.

The invention claimed is:

1. Wearable support structure (201) for at least partly relieving a human body during leaning or bending over, said structure (201) comprising a frame having:
   a chest support (202) for bearing upon a chest of said human body;
   pivoting arrangements (207) for pivoting the support structure in correspondence with the leaning or bending of the human body;
   an elongated stay (203a, 203b) connected to said chest support (202), provided to extend substantially alongside said human body and connected to said pivoting arrangements (207),
   wherein said stay (203a, 203b) is arranged such that said stay is in a first state corresponding with an upright position of said human body when being unloaded, and arranged to be biased back to said first state when being into a second state corresponding with a leaning or bending position of said human body,
   a lumbar support (204), connected to said pivoting arrangements (207), and arranged for bearing upon a lumbar area of said human body, and
   a thigh support (214), connected to said pivoting arrangements (207), and arranged for bearing upon a front side of a thigh area of said human body,
   characterized in that said wearable support structure (201) comprises a connecting device (1, 101) for detachably connecting at least one of:
   said thigh support (214) to said pivoting arrangements (207);
   said elongated stay (203a, 203b) to said chest support (202); and
   said elongated stay (203a, 203b) to said pivoting arrangements (207),
   wherein said connecting device (1, 101) comprises a first connecting element (3, 103) and a second connecting element (5, 105),
   wherein said first connecting element (3, 103) is arranged for rigid connection to a first part of said wearable support structure (201) that is at least one of said pivoting arrangements (207) and said chest support (202),
   wherein said second connecting element (5, 105) is arranged for rigid connection to a second part of said wearable support structure (201) that is at least one of said thigh support (214) and said stay (203a, 203b),
   wherein said first connecting element (3, 103) comprises a receiving wall (9, 109) that is at least partly surrounding a receiving space (11, 111) for partly receiving said second connecting element (5, 105).

2. The wearable support structure (201) according to claim 1, wherein said connecting device (1, 101) comprises a blocking unit (7, 107), wherein said blocking unit (7, 107) in a first state thereof blocks detachment of said first connecting element (3, 103) from said second connecting element (5, 105) and wherein in a second state of said blocking unit (7, 107) said first connecting element (3, 103) is detachable from said second connecting element (5, 105).

3. The wearable support structure (201) according to claim 2, wherein said first connecting element (3, 103) and said second connecting element (5, 105), while connected, extend in a longitudinal direction (A), wherein said connecting device (1, 101) comprises a rotation organ (13, 113) for allowing said first connecting element (3, 103), while connected to said second connecting element (5, 105), to rotate about a predetermined angle relative to said second connecting element (5, 105) about a common rotation axis extending in said longitudinal direction (A).

4. The wearable support structure (201) according to claim 3, wherein said predetermined angle is in the range of 60-120 degrees.

5. The wearable support structure (201) according to claim 4, wherein said predetermined angle is in the range of 80-100 degrees.

6. The wearable support structure (201) according to claim 3, wherein a rotation organ (13, 113) comprises a recess (13, 113) provided in one of said first connecting element (3, 103) and said second connecting element (5, 105), wherein said blocking unit (7, 107) in said first state of said blocking unit (7, 107) is at least partly received in said recess (13, 113) for blocking, wherein said blocking unit (7, 107) is arranged to be moveable in said recess (13, 113) for allowing rotation about said common rotation axis about said predetermined angle.

7. The wearable support structure (201) according to claim 3, wherein said blocking unit (7, 107) is arranged to be moveable in a further recess (19, 21, 119, 121) for allowing rotation about said common rotation axis about said predetermined angle.

8. The wearable support structure (201) according to claim 2, wherein said connecting device (1, 101) comprises an actuation element (23, 123) that is movable to a first position wherein said blocking unit (7, 107) is in said second state upon actuation of said actuation element (23, 123).

9. The wearable support structure (201) according to claim 2, wherein said receiving wall (9, 109) is provided with a receiving wall opening (31, 131), wherein said blocking unit (7, 107) comprises a blocking element (33, 133) that is movably arranged in said receiving wall opening (31, 131), wherein in a first position of said blocking element (33, 133) said blocking unit (7, 107) is in said first state and wherein in a second position of said blocking element (33, 133) said blocking unit (7, 107) is in said second state.

10. The wearable support structure (201) according to claim 1, wherein said connecting device (1, 101) comprises a distance organ (17, 117) for connecting said first part of said wearable support structure (201) at a predetermined distance from said second part of said wearable support structure (201).

11. The wearable support structure (201) according to claim 10, wherein said distance organ (17, 117) comprises a recess (13, 113) for connecting said first part of said wearable support structure (201) at said predetermined distance from said second part of said wearable support structure (201).

12. The wearable support structure (201) according to claim 10, wherein said distance organ (17, 117) is arranged for connecting said first part of said wearable support structure (201) at a further predetermined distance from said second part of said wearable support structure (201).

13. The wearable support structure (201) according to claim 12, wherein said distance organ (17, 117) is provided with a further recess (19, 21, 119, 121), wherein said further recess (19, 21, 119, 121) is provided in one of said first connecting element (3, 103) and said second connecting element (5, 105), wherein a blocking unit (7, 107) in a first state of said blocking unit (7, 107) is at least partly received in said further recess (19, 21, 119, 121) for connecting said first part of said wearable support structure (201) at said further predetermined distance from said second part of said wearable support structure (201).

14. The wearable support structure (201) according to claim 1, wherein said frame comprises:
a further elongated stay (203b) connected to said chest support (202), wherein said elongated stay (203a) and said further elongated stay (203b) are provided to extend substantially alongside opposite sides of said human body and connected to said pivoting arrangements (207),
wherein said elongated stay (203a) and said further elongated stay (203b) are resilient stays arranged such that they are in said first state corresponding with an upright position of said human body when being unloaded, and arranged to be biased back to said first state when being bent into said second state corresponding with a leaning or bending position of said human body, wherein said elongated stay (203a) and said further elongated stay (203b) in said first state are in a stretched state and in in said second state are in a bent state.

15. The wearable support structure (201) according to claim 14, wherein said chest support (202) comprises two spatially separated pivoting means (209a, 209b), wherein said elongated stay (203a) and said further elongated stay (203b) are each detachably connected, by said connecting device (1, 101), to said chest support (202) via a different one of said pivoting means (209a, 209b), wherein each of said pivoting means (209a, 209b) is arranged to pivot said chest support (202) with respect to a stay (203a, 203b) connected thereto, in a plane substantially parallel to said chest of said human body.

16. The wearable support structure (201) according to claim 14, wherein said two elongated stays (203a, 203b) are rotatably connected to said pivoting arrangements (207) such that the connecting ends of each of said elongated stays (203a, 203b) is rotatable around its elongated axis.

* * * * *